United States Patent [19]

Aulie et al.

[11] Patent Number: 5,139,524
[45] Date of Patent: Aug. 18, 1992

[54] PROSTHETIC ALIGNMENT DEVICE SUPPLEMENTALLY SECURED BY A HOOP STRESS

[75] Inventors: Alan L. Aulie, Indianola; Ernest M. Burgess, Mercer Island, both of Wash.

[73] Assignee: Prosthetics Research Study, Seattle, Wash.

[21] Appl. No.: 467,035

[22] Filed: Jan. 18, 1990

[51] Int. Cl.$^5$ .............................................. A61F 2/62
[52] U.S. Cl. .................................... 623/38; 623/27; 403/362
[58] Field of Search ...................... 623/38, 27; 403/362

[56] References Cited

U.S. PATENT DOCUMENTS

| 3,206,235 | 9/1965 | Albinson et al. | 623/38 X |
| 3,659,294 | 5/1972 | Glabiszewski | 623/38 |
| 3,671,978 | 6/1972 | May | 623/38 |
| 3,982,278 | 9/1976 | May | 623/38 |
| 4,161,042 | 7/1979 | Cottingham et al. | 623/38 X |
| 4,608,054 | 8/1986 | Schröder | 623/39 |
| 4,969,911 | 11/1990 | Greene | 623/38 |

FOREIGN PATENT DOCUMENTS

| 2410998 | 8/1979 | France | 623/38 |
| 0721094 | 3/1980 | U.S.S.R. | 623/38 |
| 1026803 | 7/1983 | U.S.S.R. | 623/38 |
| 1391642 | 4/1988 | U.S.S.R. | 623/33 |
| 1563246 | 3/1980 | United Kingdom | 623/38 |

OTHER PUBLICATIONS

P. Kohler et al., "A new in-built device for one-point stepless prosthetic alignment," *Prosthetics and Orthotics International* 12:103-104, 1988.
Advertisement by Hosmer Dorrance Corporation, *Journal of Prosthetics and Orthotics* 1:20, Apr. 1989.
Advertisement by United States Manufacturing Company, *American Orthotic and Prosthetic ALMANAC,* Nov. 1989, p. 39.

*Primary Examiner*—Randall L. Green
*Assistant Examiner*—D. H. Willse
*Attorney, Agent, or Firm*—Seed and Berry

[57] ABSTRACT

A prosthetic alignment device having a shank member, an alignment body, and setscrews to adjust the angular orientation of the shank member and secure the shank member in place relative to the alignment body. The alignment body has a body cavity into which the shank member is inserted, a concave bearing surface for engaging a spherical radius of curvature of the end of the shank member, and an annular opening for inserting the end of the shank member. Angulation of the shank member inside the body cavity causes the annular opening to elastically deform and exert a hoop stress on the shank member increasing the securing force therebetween.

14 Claims, 3 Drawing Sheets

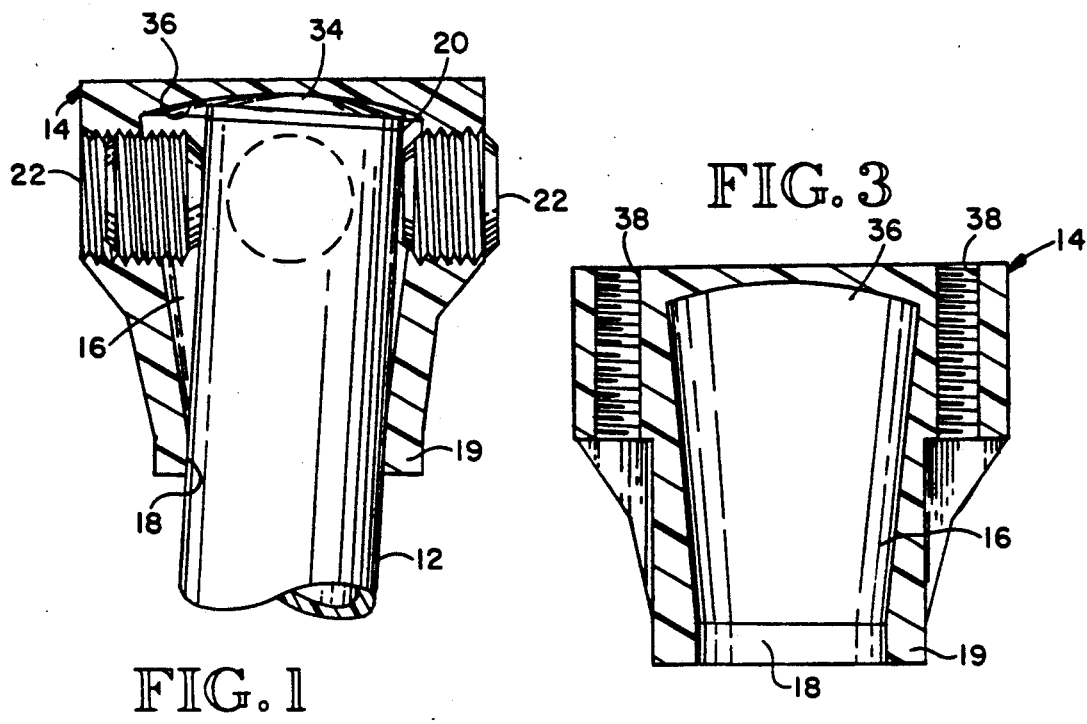
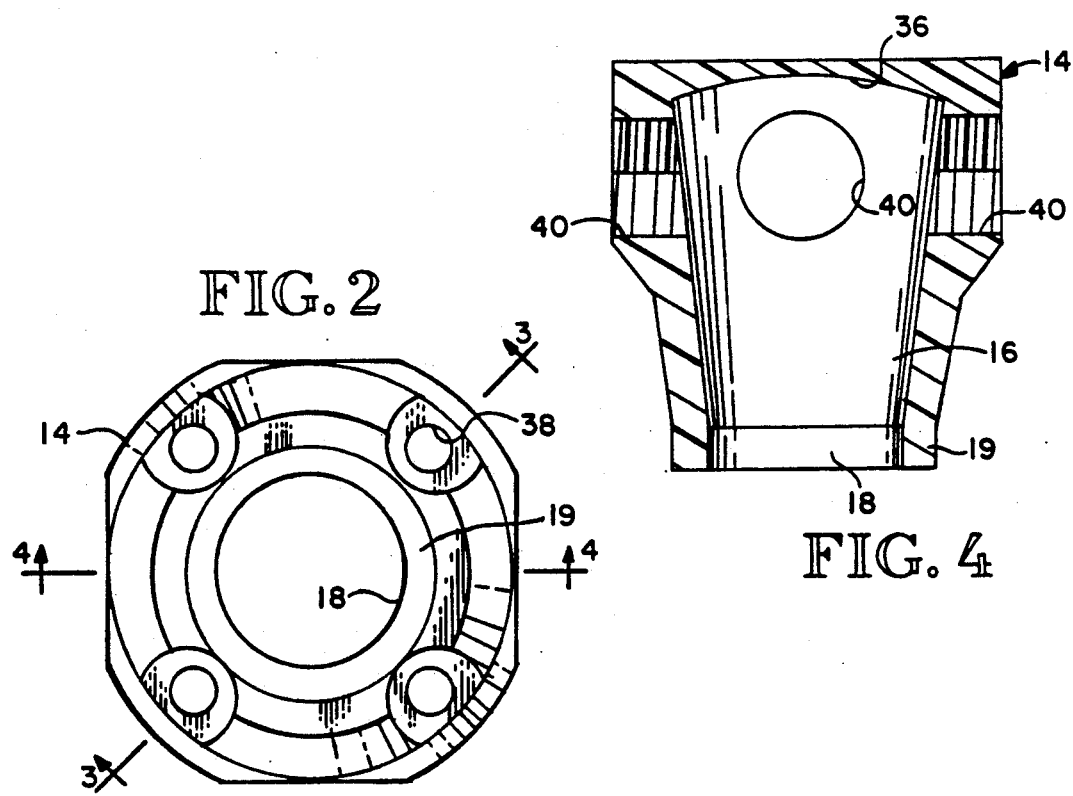

NORMAL

FLEXION

EXTENSION

NORMAL

ABDUCTION

ADDUCTION

PROSTHETIC ALIGNMENT DEVICE SUPPLEMENTALLY SECURED BY A HOOP STRESS

GOVERNMENT RIGHTS

This invention was made with the support of the United States Government. Pursuant to Title 35 U.S.C. §202, this gives notice that the Government has certain rights in the invention when used for Governmental purposes.

1. Technical Field

This invention relates to prosthetic devices for use by amputees More specifically, this invention relates to prosthetic alignment devices for adjusting the orientation of lower-limb prosthetic leg components used by amputees.

2. Background of the Invention

Lower-limb prosthetic devices, such as legs and joints, are used by amputees to help them obtain full mobility to walk, run, and jump normally. To achieve this mobility, it is essential that the prosthetic limbs and joints be aligned properly so that the prosthetic device fits snugly on the stump of the amputee, and the foot impacts the ground squarely and evenly.

Prosthetic alignment devices are used in conjunction with all prosthetic legs. Traditionally, certain alignment devices have been used as a jig to establish correct alignment of the prosthesis, and then removed while the limb is being constructed. Other types of alignment devices are manufactured to remain in the prosthetic limb as a permanent feature.

Prior prosthetic alignment devices have generally been constructed of metals and have included many machined parts and standard machine elements Such alignment devices are inherently heavy, complicated to use, expensive to manufacture, and subject to corrosion. In addition, the multiple parts used in these prior alignment devices have increased the frequency of breakdowns and needed repairs

SUMMARY OF THE INVENTION

The invention includes a prosthetic alignment device made of a lightweight, noncorrosive, resilient material which is easy to adjust The alignment device comprises a shank member having an end, an alignment body having an annular opening and a body cavity into which the end of the shank member extends, and adjustment members for adjusting the angle of the shank member relative to the alignment body.

In one embodiment, the end of the shank member includes a spherical radius of curvature which engages a concave bearing surface on the top wall of the body cavity. The width of the bearing surface is greater than the width of the spherical radius of curvature to allow angulation of the shank member within the limits of the body cavity while under a vertical axial load.

The body cavity of the alignment body has downwardly converging sidewalls forming the annular opening into which the end of the shank member is inserted. The larger end of the body cavity allows for angulation of the end of the shank member.

Setscrews or other adjustment members are inserted through the wall of the alignment body to engage the top of the shank member to angulate the shank member. The setscrews are positioned opposite each other, with one setscrew forcing the end of the shank member in one direction and another setscrew providing an opposite, resisting force to clamp the shank into a fixed position.

Angulation of the end of the shank member causes the annular opening to elastically deform to exert a hoop stress on the shank member, which increases the securing force between the alignment body and the shank member. Once the adjustments of the angular orientation of the shank member relative to the alignment body have been completed, the prosthetic alignment device becomes a static or fixed structure

BRIEF DESCRIPTION OF THE DRAWINGS

FIG. 1 is a side view, partly in section, of a prosthetic alignment device embodying the principles of the invention.

FIG. 2 is a bottom view of the alignment body.

FIG. 3 is a sectional view of the alignment body taken along the line 3—3 of FIG. 2.

FIG. 4 is a sectional view of the alignment body taken along the line 4—4 of FIG. 2.

DETAILED DESCRIPTION OF THE INVENTION

Figure 5:
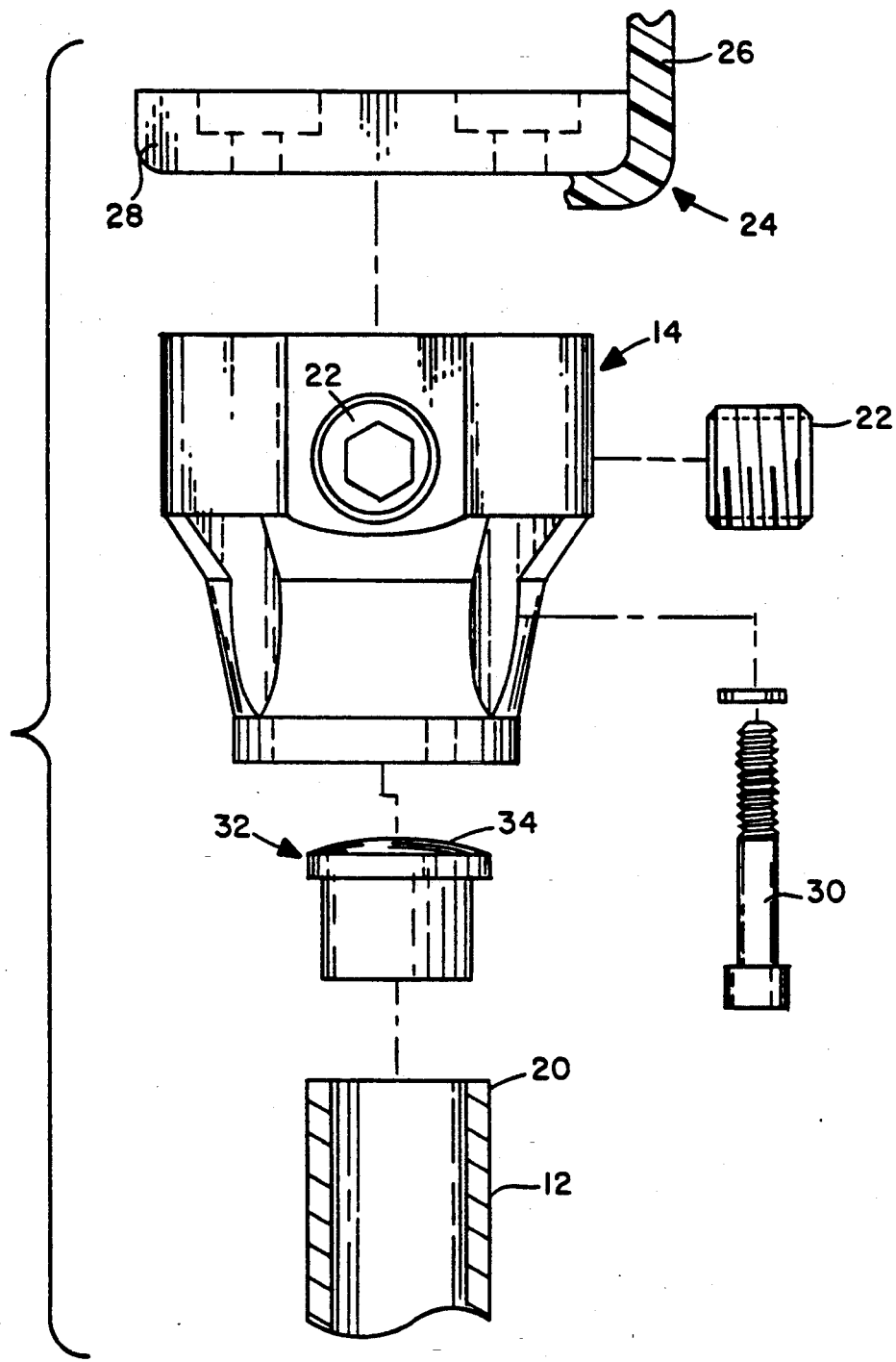
FIG. 5 is an exploded view of the alignment device with other parts of a prosthesis.

The prosthetic alignment device has few parts which can be easily adjusted. The body of the preferred alignment device is made of a polyamide material, preferably nylon or acetal resin, having low friction properties.

The alignment device is made of a plastic material capable of a minimum of 20% elongation before failing tension. One preferred material has a modulus of elasticity of approximately 400,000 psi and a tensile strength of 8,000 to 10,000 psi. One preferred material is Nylon 6/6, manufactured by Polypenco Corporation and sold under the trademark "POLYPENCO NYLON 101", an unfilled polyamide, extruded round tube of a nominal 2¼ inches in diameter. The preferred material of the alignment device weighs one-sixth of the material used in devices currently on the market and has excellent support strength.

As shown in FIG. 1, the prosthetic leg alignment device comprises a post or shank member 12 coupled to an alignment body 14 having a body cavity 16 and an annular opening 18. The diameter of the shank member 12 is fractionally larger than the diameter of the annular opening 18 to provide a slight interference fit. The shank member has an upper end 20 inserted through the annular opening and is angularly held in position by the adjusting setscrews 22.

The setscrews 22 are positioned opposite each other to provide opposite forces and clamp the shank member 12. As one setscrew is adjusted to urge the shank member toward a wall of the body cavity 16, another opposite setscrew must be retracted to maintain the desired angular orientation of the shank member. Therefore, adjustment of the setscrews must be done in pairs. The setscrews are positioned on the device so as to be accessible externally so that the alignment device can be adjusted while under a vertical axial load, perhaps by the amputee himself. Pairs of the setscrews are positioned perpendicularly to one another to provide adjustment in both the forward-backward and side-to-side directions. The opposed pairs of setscrews provide positive stops to fix the angular position of the shank member.

Adjustment of the setscrews 22 causes the end 20 of the shank member 12 to angulate, which results in elastic deformation of the annular opening 18. This deformation causes annular opening 18 to exert a hoop stress on the outside of the shank member, increasing the securing force between the alignment body 14 and the shank member. Once adjustments have been completed, the alignment device remains a static structure.

Referring to FIG. 5, the alignment body 14 is coupled to an upper socket 24, which is intended to receive the stump of an amputee. The upper socket includes a socket wall 26 and an upper socket attachment plate 28 coupled to the top, or proximal, side of the alignment body by attachment screws 30.

In one embodiment, the shank member 12 comprises a hollow tubular member made of a polyamide material. Alternatively, the shank member could be made of aluminum, wood, or other suitable material. A plastic end button 32 is inserted into the end of the shank member to cap the end opening. The end button has a spherical radius of curvature 34.

Referring now to FIGS. 2-4, the alignment body 14 has a concave bearing surface 36, generally having the same radius as the spherical radius of curvature 34. The alignment body also includes threaded apertures 38 for receiving attachment screws 30 for securing the alignment device to the upper socket 24, and threaded openings 40 into which the setscrews 22 are inserted to angulate the position of the shank member 12.

The body cavity 16 is closed and has conically shaped sidewalls which converge to form the annular opening 18. The conical shape of body cavity 16 allows a full 360-degree movement of the end 20 of the shank member during angulation.

The concave bearing surface 36 has a width greater than the width of the spherical radius of curvature 34. In one embodiment, the end button 32 engages the concave bearing surface to support the vertical load of the amputee's weight. The greater width of the concave bearing surface ensures engagement with the spherical radius of curvature while the angular orientation of the shank member 12 is adjusted in any direction within the limits of the body cavity 16. This engagement allows the shank member to be angulated while the alignment device is under a vertical axial load.

The annular opening 18 has thick wall sections 19 and has a diameter slightly smaller than the diameter of the shank member 12 to ensure a tight fit between the shank member and the annular opening. This slight interference fit causes the annular opening to deform into an oval shape upon any angulation of the shank member inside the body cavity 16, and exerts a hoop stress on the outside of the shank member, which, in turn, increases the securing force between the shank member and the alignment body 14.

The full range of angulation allows adjustment of the angular orientation of shank member 12 relative to alignment body 14 in the lateral, medial, posterior, and anterior directions.

The preferred alignment device allows for a suitable amount of elastic deformation of annular opening 18, which has been determined to allow for approximately six degrees of pivotal movement in any direction of the shank member 12 relative to a vertical axis. This angular movement will produce approximately 5 percent elastic elongation of the opening.

Figure 6:
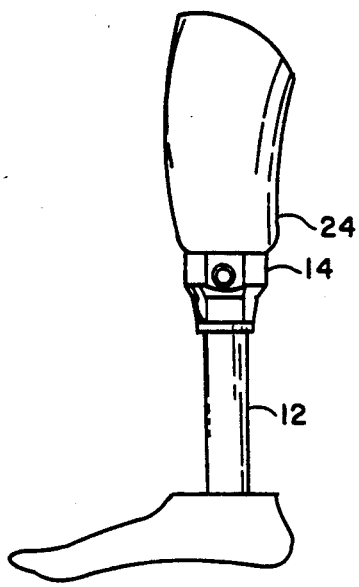
FIGS. 6, 7, and 8 are side views of the alignment device incorporated into a complete prosthetic lower leg which show how adjustments can achieve a neutral position, flexion, and extension.
Figure 7:
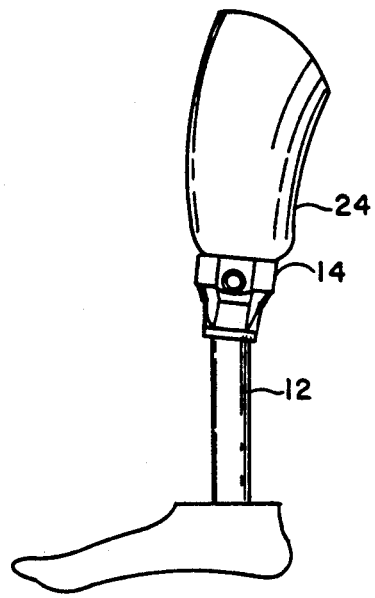
Figure 8:
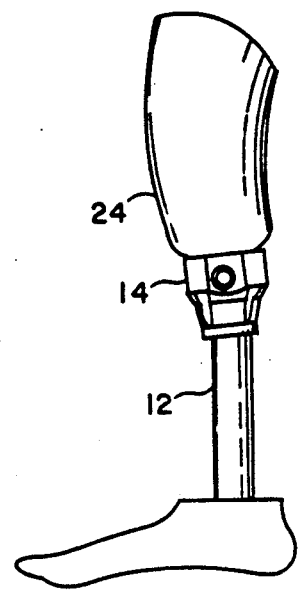

The alignment device can be adjusted to accommodate any variation in the forward-backward orientation of the stump. Adjustments in the normal direction, in flexion, and in extension, as shown in FIGS. 6, 7 and 8, respectively, can be made to provide proper forward-backward alignment of the device with the amputee's stump.

Figure 9:
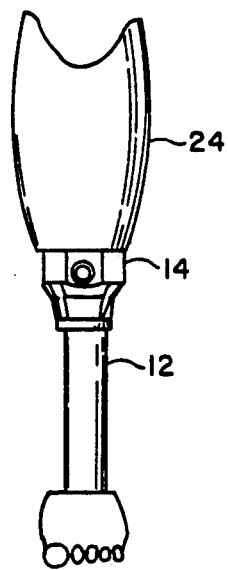
FIGS. 9, 10, and 11 are front views of the alignment device incorporated into a complete prosthetic lower leg, showing how adjustments can achieve a neutral position, abduction, and adduction.
Figure 10:
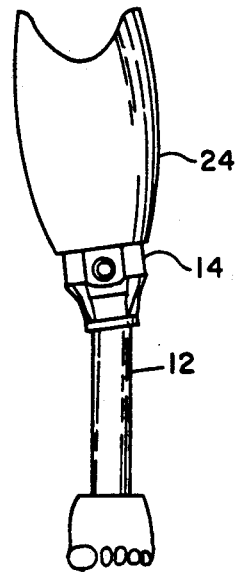
Figure 11:
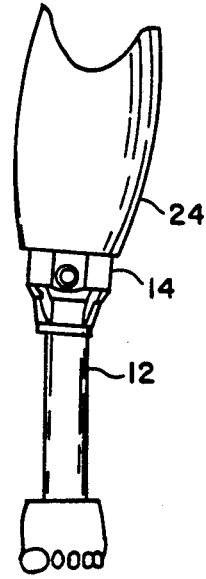

FIGS. 9, 10, and show how the alignment device can be adjusted to account for side-to-side variations in the amputee's stump. The alignment device can be adjusted to secure the prosthetic leg in the normal position, or compensate for abduction or adduction While the figures show an alignment device for use below the knee, the present invention can be used with all lower-limb endoskeletal prostheses, possibly including the hip.

While the preferred embodiments of the invention have been illustrated and described, it should be understood that variations will be apparent to one of ordinary skill in the art. Accordingly, the invention is not to be limited to the foregoing illustrations and drawings.

We claim:

1. An endoskeletal, lower prosthetic alignment device, comprising:
   an elongated shank member having an end;
   an alignment body coupled to said shank member, said alignment body having an annular opening and a closed body cavity into which said end of said shank member extends, said end of said shank member abutting said closed body cavity;
   securing means directly engaging said shank member for adjustably securing said shank member end within said body cavity and adjusting the angular orientation of said shank member relative to said alignment body;
   an upper socket into which an upper limb attaches and means for connecting said alignment body to said upper socket, said body cavity having an end bearing surface axially spaced from said annular opening, said shank member having a transverse abutment surface and being inserted through said annular opening and into said body cavity such that the transverse abutment surface of said end abuts said bearing surface of said body cavity, said annular opening creating an interference fit with said shank member at said annular opening spaced axially from said cavity end bearing surface; and
   wherein said annular opening is made of an elastic material whereby angulation of said shank member causes said annular opening to elastically deform and exert a hoop stress on said shank member which increases the securing force between said shank member and said alignment body.

2. An endoskeletal, lower prosthetic alignment device, comprising:
   an elongated shank member having an end;
   an alignment body coupled to said shank member, said alignment body having an annular opening and a closed body cavity into which said end of said shank member extends, said end of said shank member abutting said closed body cavity;
   securing means directly engaging said shank member for adjustably securing said shank member end within said body cavity and adjusting the angular orientation of said shank member relative to said alignment body;

an upper socket into which an upper limb attaches and means for connecting said alignment body to said upper socket, said body cavity having an end bearing surface axially spaced from said annular opening, said shank member having a transverse abutment surface and being inserted through said annular opening and into said body cavity such that the transverse abutment surface of said end abuts said bearing surface of said body cavity, said annular opening creating an interference fit with said shank member at said annular opening spaced axially from said cavity end bearing surface;

wherein said shank member abutment surface is spherical and said body cavity bearing surface is concave, said spherical surface engaging said concave bearing surfaces to support a vertical axial load;

wherein said spherical abutment surface comprises an end button attached to said end of said shank member, said end button engaging said concave bearing surface;

wherein said securing means comprises a plurality of setscrews threadably extending through said alignment body and engaging said shank member;

said setscrews forcing said end of said shank member toward a wall of said body cavity and clamping the shank member to change the angular orientation of said shank member relative to said alignment body for adjusting in flexion, extension, abduction, and adduction;

said setscrews being accessible externally to adjust said alignment device while under a vertical axial load;

said annular opening being made of an elastic material whereby angulation of said shank member causes said annular opening to elastically deform and exert a hoop stream on said shank member which increases the securing force between said shank member and said alignment body; and said abutment surface of said shank member being of a smaller width than the width of said concave bearing surface to ensure full angulation and constant support of a vertical axial load.

3. A prosthetic alignment device, comprising;
upper limb means, lower limb means, and alignment means for pivotally interconnecting the upper and lower limb means;
one of said limb means having a first curved bearing surface;
said alignment means including a cavity having an annular opening and a closed end with a second curved bearing surface;
said first bearing surface slidably abutting the second bearing surface;
means for adjustably fixing the angular position of the first curved bearing surface relative to the second curved bearing surface for angularly positioning the limb means relative to the alignment means; and
said limb means and said alignment means having an interference fit between one another at said annular opening whereby pivoting said limb means relative to said alignment means elastically deforms said annular opening 4. A prosthetic leg alignment device, comprising:
an elongated shank member having an end, said end having a spherical radius of curvature;
an alignment body coupled to said shank member, said alignment body having an annular opening, a body cavity into which said end extends, and a bearing surface opposite said annular opening, said annular opening being made of an elastic material and having a diameter slightly smaller than the diameter of said shank member for providing a sliding fit, said radius of curvature of said end engaging said bearing surface to support a vertical axial load; and
a plurality of equidistantly, circumferentially spaced setscrews threadably extending through said alignment body and engaging said shank member, said setscrews adjusting the angular orientation of said shank member by forcing said end toward an inside wall of said body cavity, which causes said annular opening to elastically deform, said setscrews clamping said shank member in place relative to said alignment body.

5. A prosthetic leg alignment device as recited in claim 4, wherein said annular opening upon elastic deformation exerts a hoop stress on said shank member which increases the securing force between said alignment body and said shank member.

6. A prosthetic leg alignment device as recited in claim 4, wherein said setscrews are accessible externally to adjust the angular orientation of said shank member while under a vertical axial load.

7. A prosthetic leg alignment device as recited in claim 4, wherein said end of said shank member comprises an end button, the spherical surface on said end button engaging said bearing surface.

8. A prosthetic leg alignment device according to claim 4, further comprising an upper socket into which an upper limb attaches, means for connecting said alignment body to said upper socket, and a lower prosthesis connected to said shank member.

9. An endoskeletal, lower prosthetic alignment device, comprising:
an elongated shank member having an end with a transverse abutment surface;
an alignment body coupled to said shank member, said alignment body having an annular opening and a body cavity with an end bearing surface axially spaced from said annular opening, said shank member being inserted through said annular opening and into said body cavity such that the transverse abutment surface of said end abuts the bearing surface of said body cavity to provide a bearing surface for an axial load, said shank member being slightly larger in diameter than said annular opening to create an interference fit between the shank member and the annular opening at said annular opening spaced axially from said cavity end bearing surface;
securing means adjustably securing said shank member within said body cavity and articulating said shank member relative to said body cavity to adjust the angular orientation of said shank member; and
said annular opening being elastically deformed upon articulation of said shank member which exerts a hoop stress on said shank member to secure said shank member in position relative to said alignment body.

10. An alignment device according to claim 9 wherein said shank member has a uniform transverse cross sectional area.

11. An alignment device according to claim 9 wherein said alignment body is made of plastic which allows the annular opening to elastically deform and create said hoop stress.

12. An alignment device according to claim 9 wherein the hoop stress increases as the degree of articulation of the shank member increases.

13. An alignment device according to claim 9, wherein said annular opening is spaced at least more than one shank diameter from said end bearing surface of said body cavity.

14. The alignment device of claim 13 wherein the shank member has a uniform diameter, the alignment body being made from plastic having an elasticity to deform and create the hoop stress acting on the shank member.

* * * * *